(12) United States Patent
Henkes et al.

(10) Patent No.: US 11,963,895 B2
(45) Date of Patent: Apr. 23, 2024

(54) DEVICE FOR INTRODUCING IMPLANTS

(71) Applicant: Phenox GmbH, Bochum (DE)

(72) Inventors: Hans Henkes, Stuttgart (DE); Ralf Hannes, Dortmund (DE); Hermann Monstadt, Bochum (DE)

(73) Assignee: phenox GmbH, Bochum (DE)

( * ) Notice: Subject to any disclaimer, the term of this patent is extended or adjusted under 35 U.S.C. 154(b) by 691 days.

(21) Appl. No.: 17/048,975

(22) PCT Filed: Apr. 16, 2019

(86) PCT No.: PCT/EP2019/059783
§ 371 (c)(1),
(2) Date: Oct. 19, 2020

(87) PCT Pub. No.: WO2019/201905
PCT Pub. Date: Oct. 24, 2019

(65) Prior Publication Data
US 2021/0307944 A1    Oct. 7, 2021

(30) Foreign Application Priority Data
Apr. 20, 2018    (DE) .......................... 102018109580.5

(51) Int. Cl.
*A61F 2/95* (2013.01)
(52) U.S. Cl.
CPC ......... *A61F 2/95* (2013.01); *A61F 2002/9511* (2013.01)
(58) Field of Classification Search
CPC ................ A61F 2/95; A61F 2002/9511; A61F 2002/9505; A61F 2250/0071
See application file for complete search history.

(56) References Cited

U.S. PATENT DOCUMENTS 6,716,238 B2 *  4/2004  Elliott .................... A61F 2/958
                                                        623/1.11
2002/0151967 A1  10/2002  Mikus et al.
(Continued)

FOREIGN PATENT DOCUMENTS

AR        100569      10/2016
CN      104168860    11/2014
(Continued)

OTHER PUBLICATIONS

International Search Report dated Jul. 26, 2019 from IA PCT/EP2019/059783.
(Continued)

*Primary Examiner* — Katherine M Rodjom
(74) *Attorney, Agent, or Firm* — Crockett & Crockett, PC; K. David Crockett, Esq.; Niky Economy Syrengelas, Esq.

(57) ABSTRACT

A device (1) for introducing endovascular implants (3), which have an at least partially cylindrical design, into blood vessels, where the implant (3) is provided in an expanded state in which the implant is placed in the blood vessel, and in a compressed state, in which the implant can be introduced into the blood vessel, and the device (1) has an elongated shaft (2), the exterior of which is releasably secured to the implant (3) in the compressed state and through which the implant (3) runs. The implant (3) has at least one respective connection point (6) to the shaft (2) proximally and distally, said connection point being thermally, chemically, or electrolytically releasable; or at least one thread (12) extends in the longitudinal direction over the implant (3) at least over a majority of the length of the implant (3) such that the implant (3) is secured to the shaft (2) in the compressed state, and the thread (12) has at least one respective connection point (10, 11) to the shaft (2) proximally and distally, at least one connection point (11) of (Continued)

the connection points being thermally, chemically, or electrolytically releasable.

15 Claims, 6 Drawing Sheets

(56) References Cited

U.S. PATENT DOCUMENTS

| | | |
|---|---|---|
| 2008/0027528 A1 | 1/2008 | Jagger et al. |
| 2010/0070015 A1* | 3/2010 | Schneider ............... A61F 2/958 |
| | | 623/1.42 |
| 2010/0331948 A1 | 12/2010 | Turovskiy et al. |
| 2012/0191175 A1* | 7/2012 | Costa ..................... B21F 15/06 |
| | | 623/1.15 |
| 2012/0265293 A1 | 10/2012 | Jones et al. |
| 2016/0206455 A1 | 7/2016 | Monstadt et al. |

FOREIGN PATENT DOCUMENTS

| | | |
|---|---|---|
| WO | WO2005094727 | 10/2005 |
| WO | WO2011147567 | 12/2011 |
| WO | WO2014029835 | 2/2014 |

OTHER PUBLICATIONS

Office Action dated Mar. 8, 2023 from Argentina Patent Application No. 20190101021.
Office Action dated Nov. 30, 2023 from Chinese Patent Application No. 201980035391.1.

* cited by examiner

DEVICE FOR INTRODUCING IMPLANTS

FIELD OF THE INVENTIONS

The invention relates to a device for introducing endovascular implants of at least partially cylindrical design into blood vessels, with the implant being provided in an expanded state in which it is placed in the blood vessel and in a compressed state in which it can be introduced into the blood vessel, wherein the device has an elongated shaft on the outside of which the implant is secured in the compressed state so as to be detachable, and said shaft extending through the implant.

BACKGROUND

The placement of endovascular implants into blood vessels such as arteries, veins, aneurysms or other vascular malformations is a well-known state-of-the-art technique. In this connection, stents, for example, are implanted in a blood vessel to keep it permanently open. Other examples of such devices include occlusion coils, which are inserted into an aneurysm to fill the aneurysm and induce thrombosis, or flow diverters, which are placed in front of an aneurysm to isolate it from the blood flow. Typically, such implants are brought to the desired site and placed there with the help of a catheter, which is inserted into the blood vessel system at a suitable location. The implant may, for instance, be attached to the distal end of an insertion wire, with a detachment point being arranged between the insertion wire and the implant which corrodes when an electrical current is applied and in any case dissolves to such an extent that detachment and deployment of the implant takes place. Other detachment systems are based on the fact that a mechanical form closure provided between the implant and the device for inserting the implant is disengaged.

Especially with stents, flow diverters and similarly designed implants, which have an internally hollow cylindrical structure with a plurality of openings existing on the outer surface, the advancement of the implant through a catheter or blood vessel can be difficult. In particular, it must be ruled out that the implant undergoes buckling or compression during advancement so that it may be advisable to secure the implant at the proximal and distal ends before it is liberated. At the same time, however, the implant must be capable of being detached at the target site as safely, easily and quickly as possible. It is, therefore, the objective of the present invention to further improve the implant detachment systems known from the state of the art.

Another problem that may arise with state-of-the-art implants is that the implant ultimately remaining in the blood vessel still has points of connection provided for the attachment of the insertion device. For example, in the event of a mechanical detachment system, the connecting elements arranged on the implant that enable an effective form closure to be achieved may still be left on the implant. If the implant is inserted with the aid of an electrolytically detachable insertion wire, the implant as a rule converges closely in the direction of the proximally positioned insertion wire. In other words, after electrolytic detachment, a proximal portion remains on the implant that is not required for an effective implant function. Both such a proximal portion and the connecting elements mentioned hereinbefore may have detrimental effects after the implant has been placed, for example, by protruding into the lumen of the blood vessel and obstructing blood flow, damaging the wall of the blood vessel or causing other problems.

Moreover, in case of conventionally inserted implants where the implant is to be pushed through a microcatheter, the size of the compressed implant is naturally limited due to the fact that only a certain amount of space is available and the diameter of the implant in the compressed state cannot exceed a certain limit in relation to the inner diameter of the microcatheter. Especially for neurovascular applications microcatheters are only used up to a certain size. A device for the insertion of an implant that does not rely on the implant to be pushed through a microcatheter, but instead also allows insertion without a microcatheter being put to use, would thus open up additional freedom in the design of the implant. The implant, for example, could then be made larger or more massive or have more or thicker struts.

As proposed by the present invention, it has thus been the objective to provide a device for the insertion of implants into blood vessels that overcomes the aforementioned problems.

SUMMARY

According to the invention, said objective is achieved by the provision of a device for introducing endovascular implants of at least partially cylindrical design into blood vessels, with the implant being provided in an expanded state in which it is placed in the blood vessel and in a compressed state in which it can be introduced into the blood vessel, wherein the device has an elongated shaft on the outside of which the implant is secured in the compressed state so as to be detachable, and said shaft extending through the implant, wherein the implant has at least one connection point each to the shaft on the proximal and distal side, said connection point being thermally, chemically or electrolytically detachable.

The inventive device is characterized by an elongated shaft on the outside of which the implant is arranged in its compressed state. The implant is provided proximally and distally with at least one connection point to the shaft, which can be detached to set the implant free. The device including the elongated shaft and the implant mounted on it can thus be advanced to the desired position. Preferably, the shaft is advanced distally without a catheter, i.e. the shaft is usually first advanced through a guiding catheter of relatively large lumen but using a small-lumen microcatheter for the advancement to more distally located regions is refrained from. In principle, however, it is also conceivable to use one catheter for the entire advancement, in which case at least the portion of the shaft carrying the implant is pushed out of the catheter or the catheter is retracted to such an extent that the implant is exposed.

Because of the connection points existing between implant and shaft, an implant detachment does take place initially. The position of the implant may instead be changed arbitrarily by moving the shaft, should the attending physician decide that repositioning is required. If necessary, the shaft carrying the implant may also be retracted in proximal direction, completely repositioned or removed from the blood vessel system.

In the event the treating physician has decided to detach the implant, the connection points between shaft and implant are disengaged. This can be done thermally, chemically or electrolytically. As soon as the connection points are disengaged, the inherent expansion tendency of the implant ensures that it assumes its expanded state in which it is to be deposited within the blood vessel. Following this, the shaft and, if applicable, the catheter can be retracted in proximal direction and finally removed from the blood vessel system while the implant remains at its placement site.

The terms "proximal" and "distal" are to be understood such that they refer as proximal to parts that point towards the attending physician when inserting the device, and as distal to parts that point away from the attending physician. Typically, the device is thus pushed forward through the blood vessel or a catheter in distal direction. The term "axial" refers to the longitudinal axis of the device extending from proximal to distal while the term "radial" denotes levels/planes extending vertically thereto.

To ensure the inherent expansion tendency of the implant is utilized, it is considered expedient for the implant to have self-expanding properties. For that reason, the implant is preferably made of a shape memory material, as it is basically known for the manufacture of stents and similar components. Therefore, shape memory alloys are particularly suitable as materials for this application, for example binary nickel-titanium alloys (e.g. nitinol) or ternary nickel-titanium-chromium and nickel-titanium-copper alloys. Nitinol in particular is known for applications in the medical field in self-expanding structures. Nevertheless, other shape memory materials such as other alloys or shape memory polymers are also conceivable.

The implant, which has an at least partially and preferably completely cylindrical shape, is as a rule provided with openings distributed over the surface of the cylinder. In other words, a lattice or mesh structure is thus formed that is made up of struts or braces, so that a plurality of openings or meshes are created on the outer surface of the cylinder.

The term "opening" refers to the lattice structure, regardless of whether the opening is separated from the environment by a membrane, meaning, even an opening that is covered by a membrane is referred to as opening. If required, a membrane can be applied to the outside or inside of the grid/lattice structure. It is also possible to embed the grid/lattice structure in a membrane.

The lattice structure of the implant may be a braided structure, that is, may consist of individual wires or wire bundles forming struts which are braided together and at the points of intersection of the wires/wire bundles extend above and below each other. Likewise, a cut structure can be put to use in which the lattice structure is cut out of a tube of suitable diameter by means of a laser. The material usually consists of metal, however plastic material may be employed as well. The material must have sufficient elasticity to allow contraction to the diameter of the shaft and, moreover, bring about the expansion to the desired diameter when liberated. Moreover, it is expedient to electropolish the lattice structure to make it smoother and more rounded and thus render it less traumatic. This also reduces the risk of germs or other impurities that may adhere to the structure. The struts or wires may have a round, oval, square, rectangular or trapezoidal cross section, with the edges being advantageously rounded off in the event of a square, rectangular or trapezoidal cross section. Flat webs/wires in the form of thin strips, especially metal strips can be employed as well.

For the implant provided as a component of the device proposed by the present invention different implant types can be used which are basically known from the state of the art. As a prerequisite, however, the implant must have an internal cavity so that the elongated shaft can pass through the implant and the implant is mounted on the shaft. Examples of such implants include stents, flow diverters or other implants that are to be placed in front of an aneurysm or other vascular malformations in order to influence the flow of blood. This also includes implants that are intended for placement in the area of bifurcation aneurysms, as they have been described for example in publication WO 2014/029835 A1.

As a rule, the implant as component of the inventive device has a length ranging between 5 mm and 100 mm and a diameter between 1.5 mm and 7 mm, the dimensions being determined by the dimension of the vessel segment. The figures indicated refer to the free, non-compressed state of the implant, that is, detached from the shaft and without the catheter exerting any external force. The struts forming the implant may, for example, have a width, respectively diameter ranging between 20 and 60 µm.

A major advantage of the inventive device is the fact that the implant can also be brought to its placement site without a microcatheter being put to use so that the implant thus being subject to fewer limitations in size. In addition, the implant remains proximally and distally secured until it is detached, so there is no risk of buckling, stretching or kinking when the implant is advanced through a vessel or a catheter. Furthermore, another advantage is that essentially only the actual implant with its components that are needed to achieve the intended effect remains in the blood vessel, and not, after detachment, any technically superfluous elements provided as means of connection to the insertion wire or to some other insertion device. This can be important, for example, if only a comparatively short section of the blood vessel is available in which the implant can be placed without affecting or impairing any branching blood vessels.

The implant is provided proximally and distally with at least one connection point to the shaft. Preferably, the connection points may each be located at the distal and proximal ends of the implant, but it is also conceivable to arrange the connection points in the proximal and distal region of the implant, however, situated a slight distance away from the respective end of the implant. The implant should preferably be fixed to the shaft essentially over its entire length before detachment occurs.

To prevent a partial detachment of the implant from the shaft, it is seen as an advantage if the implant has at least two connection points to the shaft both proximally and distally, preferably arranged at the proximal and distal ends of the implant. If required or thought useful, even more connection points may be provided to achieve a comprehensive fixation around the radial circumference of the implant on the shaft. Additionally, connection points may also be provided between the proximal and distal end of the implant. However, due to the fact that the implant is securely positioned on the shaft in an elongated configuration and is retained in this configuration by proximally and distally arranged connection points, no further connections are generally needed between the proximal and distal ends.

In accordance with an alternative embodiment, to which the considerations stated hereinbefore also apply, in particular with regard to the structure and material of the implant, a device is provided for the introduction of endovascular, at least partially cylindrical implants into blood vessels, in which the implant is in an expanded state, in which it is placed in the blood vessel, and in a compressed state, in which it can be introduced into the blood vessel, wherein the device having an elongated shaft, on the outside of which the implant is detachably secured in the compressed state and with said shaft extending through the implant, wherein at least one thread extends in the longitudinal direction over the implant, at least over a major portion of the length of the implant in such a way that the implant is fixed on the shaft in the compressed state, wherein the thread has at least one connection point to the shaft each proximally and distally, of which at least one connection point can be detached thermally, chemically or electrolytically.

Also in accordance with this alternative embodiment, the implant is placed on the outside of the shaft and is retained on the shaft in its compressed form until detachment occurs. However, the connection points do not connect the shaft to the implant, but instead the shaft with one or several threads that extend over the implant. Preferably, at least one thread runs spirally around the implant, that is, the thread is wound around the implant in a helical pattern, thus making sure the implant is secured on the shaft and kept in its compressed state. Otherwise, the procedure for introducing the implant is similar to the first embodiment, which means the shaft together with the implant is navigated to the desired location. In most cases, the shaft with the implant is advanced to the placement position not via a microcatheter but through the blood vessel itself. However, same as in the first embodiment of the invention, a relatively large-lumen guiding catheter is used as a rule to advance the shaft with implant, and with only the small-lumen microcatheter being dispensed with for advancement further distal. For example, in neurovascular applications the device can be advanced via the guiding catheter from the groin to the carotid artery, with any further advancement then taking place in the absence of a microcatheter.

However, it is still possible, of course, to navigate the shaft and implant to the target position through a catheter. In this case, the shaft and catheter are moved relative to each other in such a way that the implant and at least the portion of the shaft that carries the implant are no longer positioned inside the catheter.

As soon as the attending physician has decided on the final detachment of the implant, at least one of the connection points between the shaft and the thread is disengaged. This causes the thread to become loose so that it will no longer be able to hold the implant in a compressed state on the shaft. By taking advantage of its inherent expansion tendency, the implant will now widen to assume its expanded shape and thus anchor itself in the blood vessel. The shaft, which now only extends loosely through the inside of the implant, can then be easily retracted proximally and removed from the blood vessel system.

In the second embodiment, particularly the distal connection point or, in the event several threads are provided, the distal connection points located between thread and shaft are preferably designed so as to be detachable. However, the proximal connection point between thread and shaft preferably remains still in place. The distal detachment of the thread offers the advantage that when the shaft is retracted after the implant has been deployed, the thread remains proximally attached to the shaft causing it to be also retracted and thus preventing it from turning over. A turning over of the thread would entail the risk of the thread damaging the vessel wall or getting caught on the implant.

Preferably, the connection points between shaft and thread are each located at the proximal and distal ends of the thread, thus preventing areas of the thread from projecting proximally or distally beyond the respective connection point. However, it is also conceivable to arrange the connection points a certain distance away from the proximal or distal end of the thread, as long as it is ensured that the thread fixes the implant in its compressed state securely to the shaft. Expediently, the thread extends over the entire length of the implant, preferably be arranged spirally around the implant.

In both the first and the second embodiment of the invention, the connection points may be of thermal, chemical or electrolytic design, that is, the connection points can be dissolved by thermal action, by chemical action, in particular by the application of a solvent, or electrolytically by the application of an electric voltage at least to such an extent that the implant, respectively the thread becomes detached from the shaft. In case a thermal connection point has been provided, a heat source must be applied to the connection points to be detached in order to disconnect the implant. This can be done from the outside by running a heat source along the shaft to apply thermal energy to the connection points. Preferably, however, the shaft is of hollow design, which also enables a heat source to be brought to the connection points to be detached through the inside of the shaft. The heating of the shaft inside at the location where a connection point is arranged on the outside ensures that the connection point becomes detached.

Alternatively, it is also possible to heat the entire or a section of the shaft to such an extent that the connection points become detached and the implant is released.

In the event of a thermal detachability, the connection point should be designed such that, on the one hand, no detachment occurs at body temperature and the implant is held securely on the shaft, but on the other hand, too high temperatures do not have to be applied to achieve detachment. Preferably, the at least partial dissolution of the connection point occurs at a temperature ranging between 40 and 80° C., especially between 50 and 70° C. Appropriate materials for the connection points, for example polymers or low-melting metals, are known from the state of the art.

As an alternative, the connection points can also be of adhesive design, with a polymer adhesive being preferably used. In this case, the implant or thread is detached chemically, typically by applying a solvent that at least partially dissolves the adhesive. For example, dimethyl sulfoxide (DMSO) can be employed as solvent.

In this case as well the solvent can be delivered to the connection point by different means. For example, a hose or similar appliance can be run along the outside of the shaft to apply a solvent to the connection points. However, also in case adhesive connection points are used, it is preferable to bring the solvent to the connection points via the inside of the shaft. This can be done through a hose or through a tube which is arranged inside the shaft. A prerequisite for this is, of course, that, on the one hand, the shaft has an internal cavity and, moreover, there is a certain permeability of the outer wall of the shaft, thus allowing the solvent applied on the inside to permeate through the shaft causing the adhesive connection point to become detached. Moreover, it is also possible to provide one or several solvent reservoirs in the area of the connection points, said reservoirs being externally controllable and opened in such a way that the solvent is capable of having an effect on the connection point. In principle, solvent reservoirs of this nature can also be arranged on the outside of the shaft, provided that the release the solvent can be initiated from the outside.

Another possibility is the electrolytic detachment of the connection points. In this case, the at least partial dissolution of the connection point occurs by applying an electrical voltage. In most cases, direct current is used for this, with a low current intensity (<3 mA) being sufficient. Usually, the connection point consists of metal and, upon application of an electrical voltage, forms the anode where the oxidation and thus the dissolution of the metal takes place.

The electrolytic detachment is achieved by making use of a power source to apply an electric voltage to the connection point. The electrolytic detachment of implants is well known practice in the state of the art, for example with respect to occlusion coils used for the purpose of obstructing aneurysms, cf. e.g. WO 2011/147567 A1. While the connection point serves as anode, the cathode may be positioned on the body surface, for example. Alternatively, another area of the device can also form the cathode. It is to be understood that the connection point must be connected with the power source in an electrically conductive manner. The shaft itself can be used as a conductor; alternatively, a conductor can be run through the inside of the shaft or extend along the outside of the shaft. Since with a cathode positioned on the surface of the body the arising corrosion current is controlled via the surface area of the cathode, the area of the cathode should be selected significantly larger than the area of the anode. To a certain extent the speed at which the connection point is dissolved can be controlled by appropriately sizing the cathode surface in relation to the anode surface. The device proposed by the invention can thus also comprise a voltage source and, if applicable or appropriate, an electrode that can be placed on the body surface. Suitable materials for the connection point to be electrolytically dissolved include, for example, stainless steel, magnesium, magnesium alloys or cobalt-chrome alloys.

Irrespective of the exact design of the connection points, it is preferable for the shaft to have an internal cavity extending in the longitudinal direction of the shaft, in other words to exhibit an internal lumen. On the one hand and as already mentioned, this can serve for the detachment of the connection points, on the other hand a lumen is also advantageous in that a guidewire can be provided to extend through the lumen. Accordingly, a guidewire can initially be pushed forward to the desired placement site, followed by sliding the shaft with implant over the guide wire. Once the shaft has been placed in position, the guidewire can be retracted in proximal direction. The lumen of the shaft must have a diameter that enables the shaft to be advanced over the guidewire. The internal cavity or hollow space of the shaft can extend from the proximal to the distal end of the shaft. Accordingly, the invention also relates to a combination of the device proposed by the invention with a guidewire.

If the internal cavity of the shaft extends from the proximal to the distal end and also the guidewire extends through the entire shaft, this is called an over-the-wire (OTW) system. Alternatively, a rapid exchange (Rx) system is also conceivable. In this system, the guidewire extends only through the distal section of the shaft, with the distal section typically having a length of approximately 20 to 40 cm. In this context, the shaft has an opening or through-hole located proximal to the distal section through which the guidewire passes and exits the lumen of the shaft. Such an opening or through-hole is also called a port. OTW and Rx systems, for example, are familiar to those skilled in the art in the field of balloon catheters. Even in the presence of an opening or through-hole, the shaft may be provided with an internal cavity extending from proximal to distal, which in this case primarily serves for the introduction or delivery of agents for electrolytic, thermal or chemical dissolution of the connection points, as described hereinbefore.

In the event of adhesive connection points requiring the introduction of a solvent through the inner cavity of the shaft, the shaft should be permeable to the solvent at least in the sections where the detachable adhesive connection points are located, so that the solvent can penetrate through the wall of the shaft to the outside and release the adhesive connection point. Therefore, the invention also relates to a device being provided with a delivery system for solvents, with said delivery system extending at least temporarily through the inner cavity of the shaft so that a solvent can be delivered to the locations on the inside of the shaft corresponding to the locations on the outer side where the shaft has adhesive connection points which must be detached to deploy the implant. The delivery system may be of different design; it may comprise hoses or tubes extending through the inner lumen of the shaft so that the solvent is delivered from proximal to distal through the entire or part of the shaft. Alternatively, there is no need to provide a separate tube; instead, the solvent is passed through the lumen of the shaft.

In accordance with a a preferred embodiment, the shaft is at least partially composed of a coil, which consists of a metal wire or plastic thread formed into a helical configuration. This is particularly true for the distal area of the shaft, respectively the area carrying the implant. On the one hand, the helical design ensures increased flexibility of the shaft, which is particularly advantageous when passing a shaft through highly tortuous blood vessels of narrow lumen with small curve radii, such as those found in the neurovascular field. Moreover, the interspaces between the individual windings of the coil can be designed so that they are permeable to solvents. Accordingly, in the event the connection points between the shaft and implant and/or shaft and thread are chemically dissolved, a solvent is allowed to be released inside the shaft, passes through the interspaces existing between the windings and thus cause the connection point to be detached. Additional cutouts in the shaft can therefore be dispensed with.

Various materials can be used for the coil, for example typical metals such as those used for endovascular devices. Relevant examples include stainless steel, cobalt-chrome alloys and nickel-titanium alloys. It is also possible to use plastic materials that are unobjectionable from a medical point of view.

An alternative to using a coil in the distal part of the shaft can be to provide a hose/tube material that should as well possess sufficient flexibility. Depending on which method of detachability is chosen for the connection points, additional cutouts could be arranged in the hose material that permit a solvent or also an electrical contact to be brought to the connection points to be detached.

While it is of advantage for the distal part of the shaft to be designed so as to exhibit adequate flexibility, the further proximal part of the shaft may be designed to have greater stiffness. Since the shaft must often been pushed forward over comparatively long distances within the blood vessel system, it is advisable to design the proximal area so as to be stiffer, while greater flexibility is of advantage in the distal area, which, for example when neurovascular interventions are to be performed, has to reach finely branched blood vessels of narrow lumen.

The proximal end of the shaft can, for example, consist of a conventional hub. The use of a standard luer fitting or luer-lock connector is recommended, with such a connector enabling the insertion of accessories into the interior of the shaft, for example a guidewire or means required to cause the connection points to be detached. These can be means required for the supply of a solvent, to induce heating in an area of the shaft or to apply an electrical voltage. In most cases, the inner lumen of the connector becomes narrower in the distal direction, i.e. towards the inner lumen of the shaft itself. In case a luer-lock connector is used, the connection to other elements is additionally made by means of screw fittings provided for this purpose. The connecting element can be made, for example, of polycarbonate, polyamide, polypropylene or other polymers. As a rule, the material is stiffer than the material for the actual shaft.

The invention is particularly well suited for use in the neurovascular field, but applications of the devices in other areas of the blood vessel system, for example cardiovascular and peripheral, are also possible.

Meaningfully, the device is provided with one or several radiopaque markers allowing the attending physician to visualize it. The radiopaque markers may, for example, consist of platinum, palladium, platinum-iridium, tantalum, gold, tungsten or other metals opaque to radiation. They allow the attending physician to see whether the device, and in particular the implant arranged on the shaft, is correctly positioned so that corrections can be made, if necessary. It is also conceivable to provide at least some areas of the shaft and/or the implant with a coating of a radiopaque material, for example with a gold coating. This coating can, for example, have a thickness of between 1 and 6 μm. However, even if a radiopaque coating is provided, it may be useful to additionally arrange one or more additional radiopaque markers. Another possibility is to sheathe individual struts of the implant with a helix or wire consisting of a radiopaque material such as platinum.

In addition to the device the invention proposes, the invention also relates to a method for the insertion/placement of implants into blood vessels. This method provides for the implant to be fixed on the shaft and placed into the blood vessel. In the first embodiment, all the connection points between the implant and the shaft are then detached to liberate the implant. The implant expands to assume the shape it has in the released state and anchors itself within the blood vessel. The shaft itself is no longer attached to the implant and can therefore be retracted proximally and removed from the blood vessel system.

In the second embodiment, which provides for the implant to be retained on the shaft by means of a thread, a basically similar approach is adopted, but in this case only one connection point between thread and shaft is usually detached so that the thread no longer holds the implant on the shaft in a compressed state. It may also be possible to detach several connection points between one or more threads and the shaft; it is important, however, that after detachment the thread or threads are no longer capable of compressing the implant and retaining it on the shaft, and that the expansion of the implant is ensured. Now the shaft is no longer firmly attached to the implant and can thus be proximally removed from the blood vessel system. Any and all statements made with respect to the devices shall equally apply in the same way as well to the method described herein and vice versa.

The invention is now described in detail by way of examples as follows with reference being made to the figures showing the respective embodiments. It is to be noted that the figures show preferred embodiment variants of the invention, but the invention shall not be deemed to be limited to these. To the extent it is technically expedient, the invention comprises, in general, any optional combinations of the technical features that are stated in the claims or in the description. All statements made with regard to the first embodiment of the invention with connection points between shaft and implant apply in the same way to the second embodiment with connection points between shaft and thread and vice versa, unless the context indicates otherwise.

BRIEF DESCRIPTION OF THE DRAWINGS

Elucidation of the invention is provided by the following figures where.

DETAILED DESCRIPTION

Figure 1:
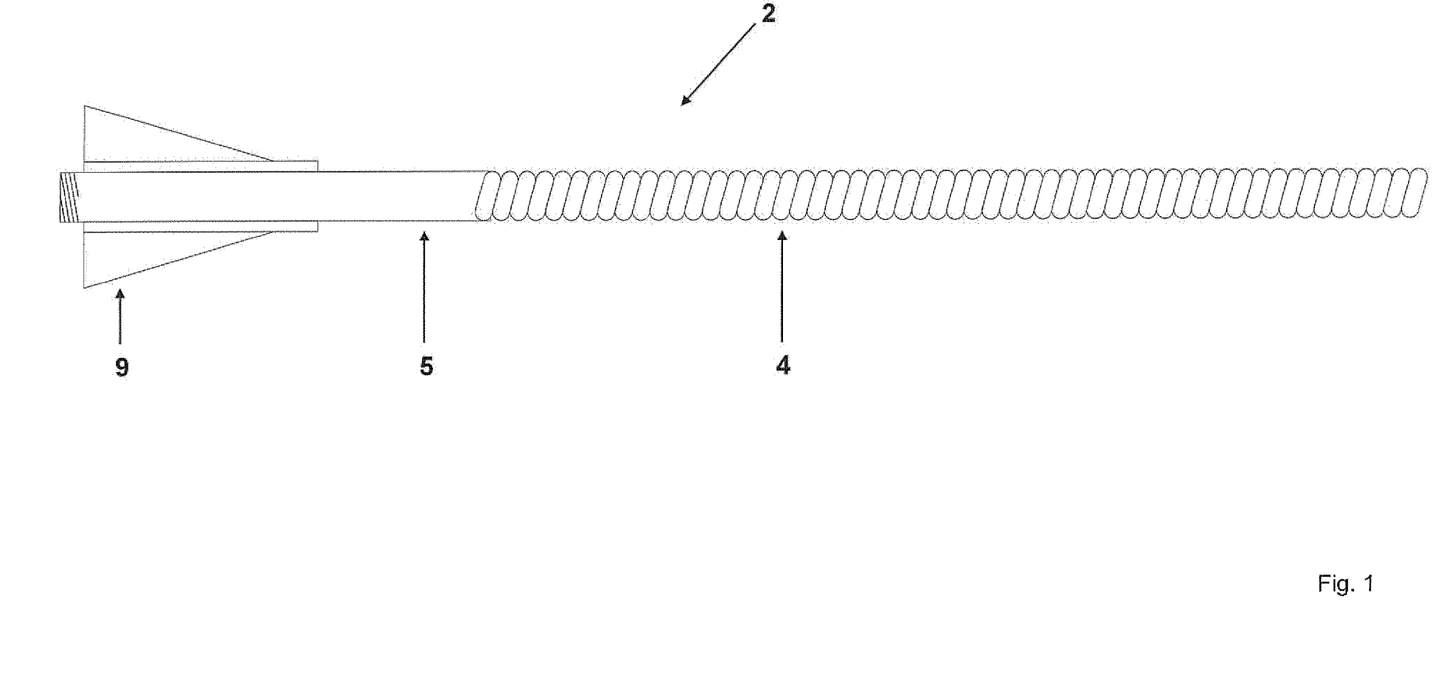
FIG. 1 is a side view showing the shaft of the inventive device.

In FIG. 1, a shaft 2, as it is part of the device proposed by the invention, is shown in side view, where in the selected representation left means proximal and right means distal. On shaft 2 there is a proximal area 5 of comparatively high stiffness and a flexible coil 4 forming the distal area of the shaft 2. The proximal end of the shaft 2 forms the connecting element 9 in the form of a threaded luer-lock connector.

Figure 2:
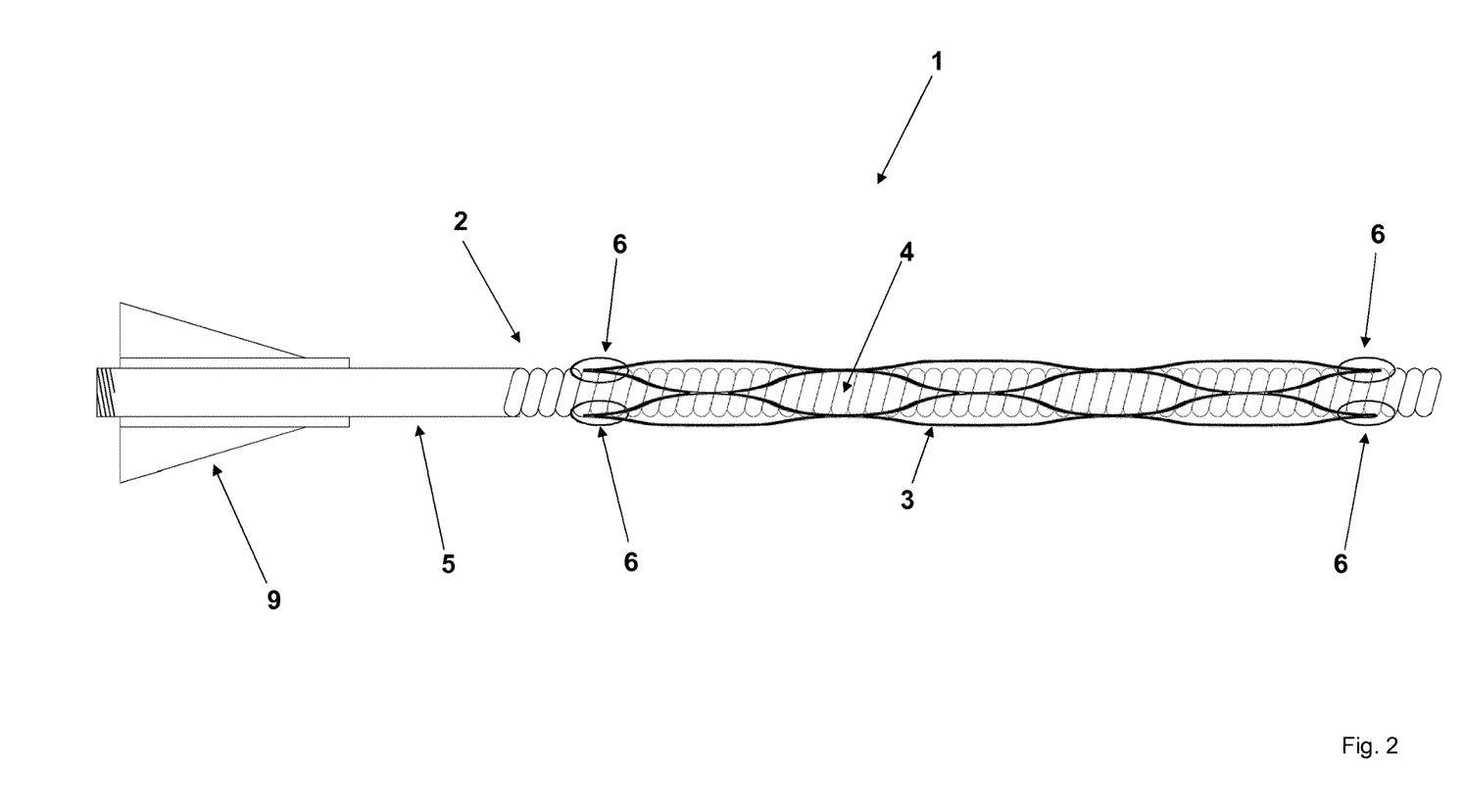
FIG. 2 shows a side view of the device proposed by the invention as per a first embodiment with the implant being fixed to the shaft.

FIG. 2 shows the device 1 according to a first embodiment. The shaft 2 in this case carries the implant 3, which consists of a laser-cut stent. Implant 3 is connected to the coil 4 of shaft 2 by means of several connection points 6. The connection points 6 are of adhesive design and can be detached by the application of a solvent. The solvent can be brought to the connection points 6 through the inside of the shaft 2, due to the fact that the interspaces between the windings of the coil 4 are sufficiently permeable.

Figure 3:
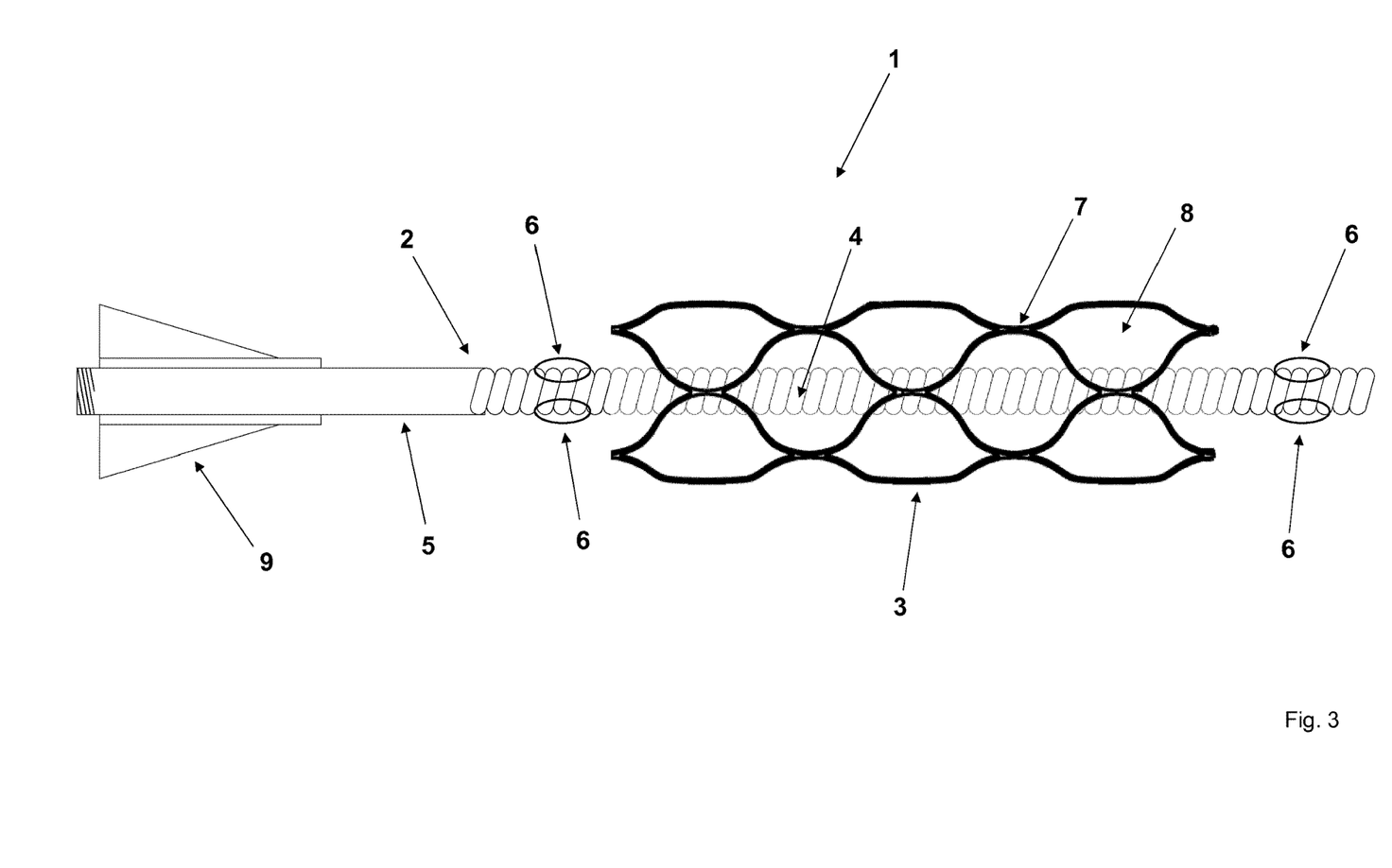
FIG. 3 illustrates a side view of the device proposed by the invention as per a first embodiment with the implant being detached from the shaft.

Once the connection points 6 have been detached, there is no longer a direct connection between implant 3 and coil 4, as can be seen from FIG. 3. Since implant 3 has self-expanding characteristics, it opens out and thus assumes its ultimate position within the blood vessel. The shaft 2, respectively the distal area of the shaft, i.e. the coil 4, extends only loosely through the interior of the implant 3 and can thus be easily retracted in the proximal direction. The implant 3 is composed of struts 7, between which openings 8 are formed.

Figure 4:
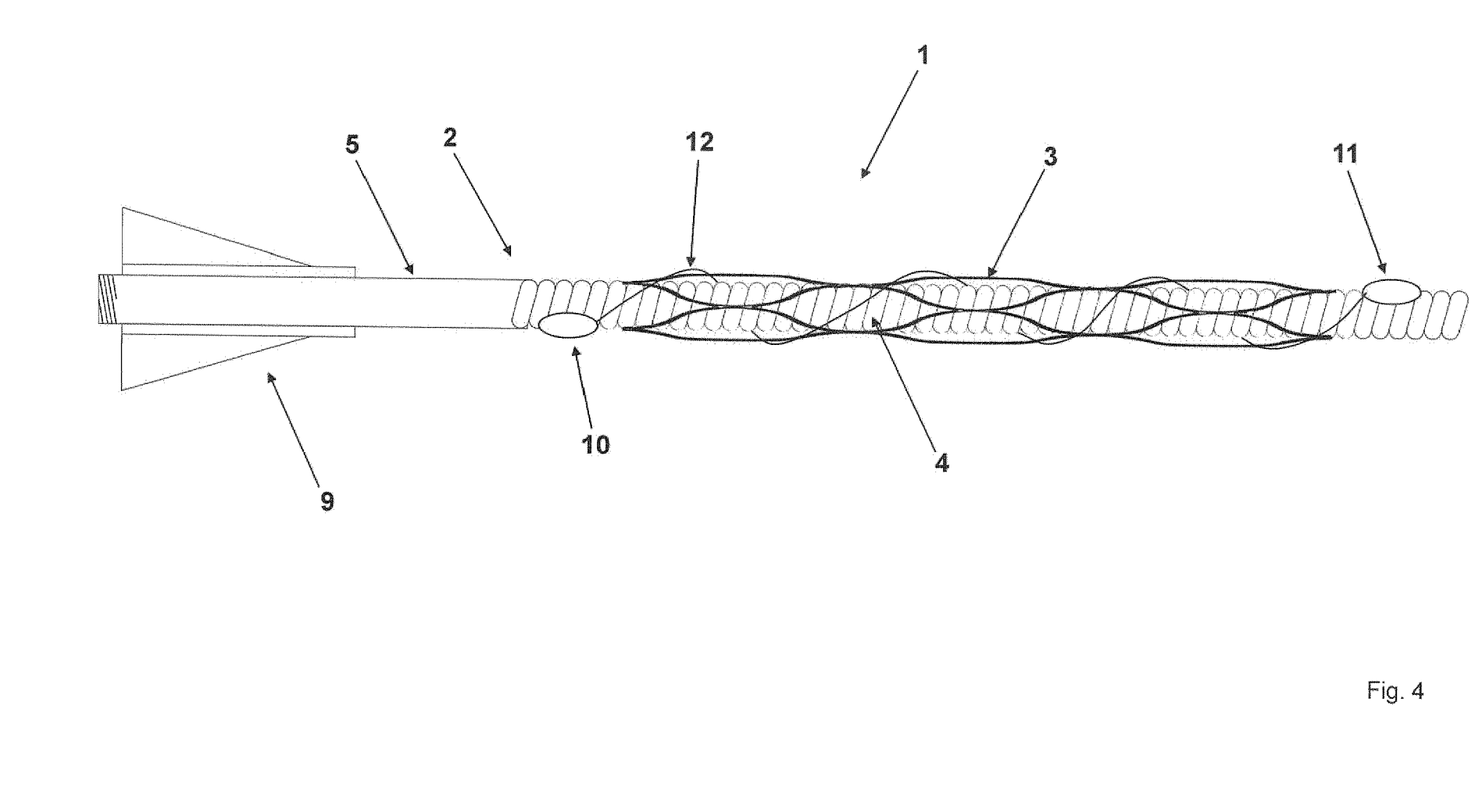
FIG. 4 shows a side view of the device proposed by the invention as per a second embodiment with the implant being secured to the shaft.

FIG. 4 shows an example of the second embodiment. In this embodiment, the implant 3 is also arranged on coil 4 that forms the distal region of the shaft 2, however, in contrast to the first embodiment the connection points do not directly connect the implant 3 with the coil 4, but, instead, a thread 12 is arranged securing the implant via connection points 10, 11. The thread 12 winds around the implant 3 and thus holds it in its compressed form on the coil 4 of the shaft 2. The implant 3 has a natural expansion tendency, but is prevented from expanding as long as thread 12 is wound around implant 3.

Figure 5:
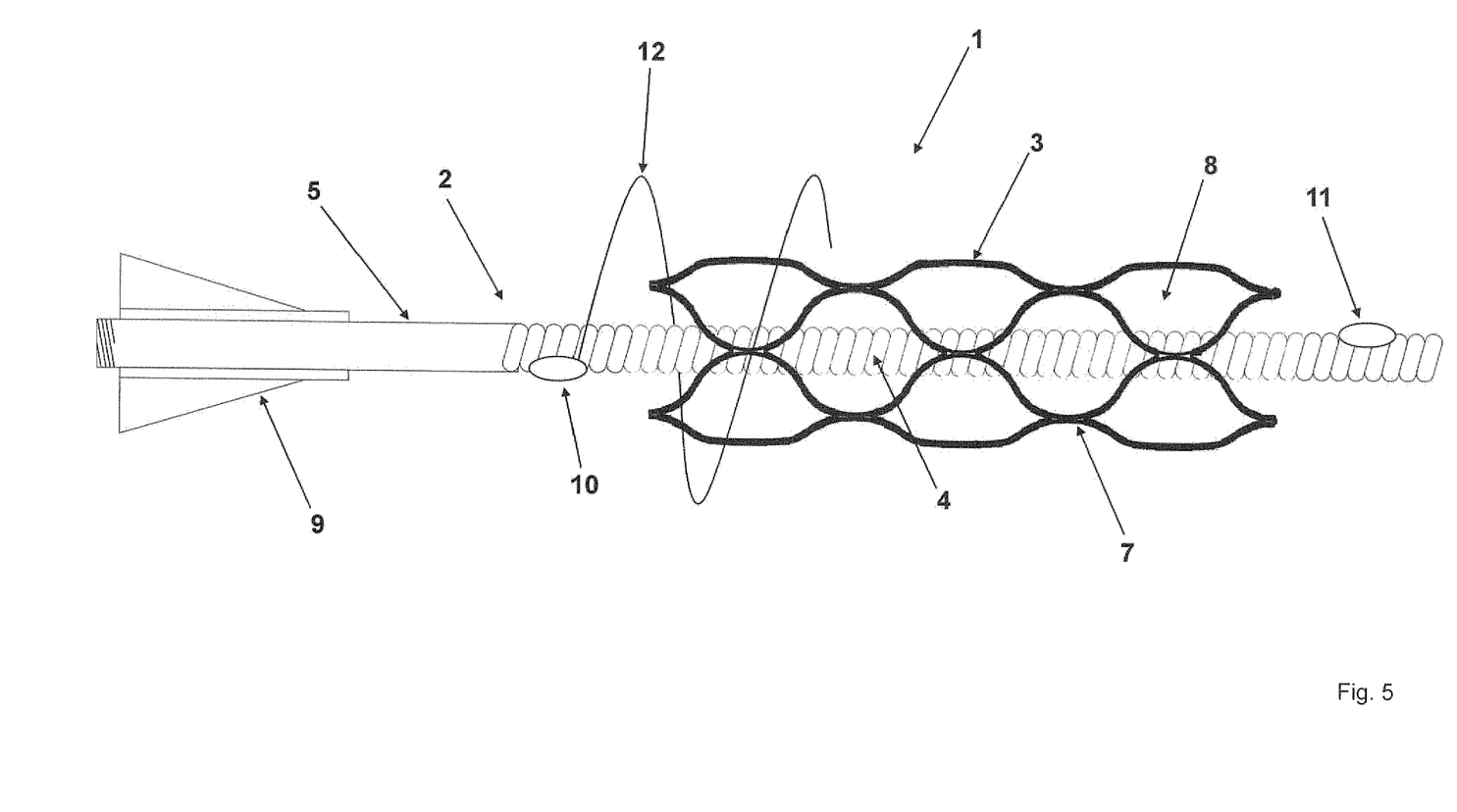
FIG. 5 illustrates a side view of the device proposed by the invention as per a second embodiment with the implant being detached from the shaft.

In FIG. 5 the deployment of the implant is illustrated as provided by the second embodiment. The distal connection point 11 has been disconnected, that is, at the distal end the thread 12 is no longer attached to the coil 4. The detachment of the connection point 11 may again be carried out in such a way that a solvent acts on the connection point 11, which is designed as an adhesive anchoring location, with the solvent penetrating the coil from inside through the interspaces located between the windings of coil 4. In contrast, the connection point 10 at the proximal end of thread 12 is retained.

As a result of the thread 12 being no longer tightly wound around implant 3, implant 3 is allowed to expand due to its shape memory properties and anchors itself in the blood vessel. The coil 4 of shaft 2 now only extends through the lumen of implant 3 without having any connection to implant 3 so that it can be retracted proximally and removed from the blood vessel system. At the same time, the thread 12, which still is firmly attached with the coil 4 at the proximal connection point 10, is also retracted in the proximal direction and removed in this manner.

Figure 6:
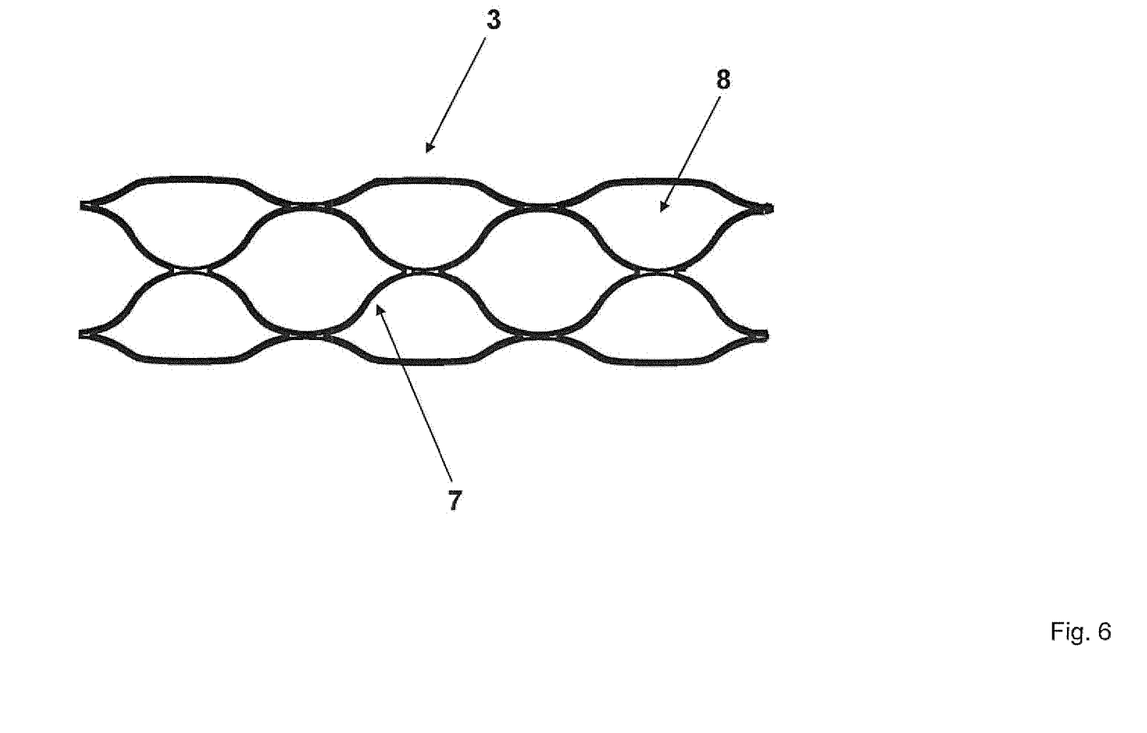
FIG. 6 shows the implant in released state.

Finally, FIG. 6 shows the deployed implant 3 that is placed into the blood vessel in this form. Implant 3 is a cut-out stent with struts 7 forming various openings 8 between them.

We claim:

1. A device for the placement of an endovascular implant of at least partially cylindrical design into blood vessels, with the implant having an expanded state in which it is placed into the blood vessel and a compressed state in which it can be inserted into the blood vessel, wherein the device has an elongated shaft on the outside of which the implant is secured in the compressed state so as to be detachable, the elongated shaft having an inner cavity or hollow space extending in the longitudinal direction of the shaft and being permeable to a solvent where adhesive connection points are located, and said shaft extending through the implant, wherein the implant has at least one connection point to the shaft proximally and at least one connection point to the shaft distally, said connection points comprising an adhesive, and being chemically detachable by contacting the connection points with a solvent that dissolves the adhesive to such an extent that the implant is detached from the shaft and further including a delivery system for solvents, which extends at least temporarily through the inner cavity or hollow space of the shaft and through which a solvent can be applied to those locations of the shaft at which adhesive connection points are arranged on the outside of the shaft.

2. The device according to claim 1, wherein at least one connection point is located at the proximal end of the implant and at least one connection point is arranged at the distal end of the implant.

3. The device according to claim 1, wherein the adhesive connection points comprise a polymer adhesive.

4. The device according to claim 1, wherein the inner cavity or hollow space extends from the proximal to the distal end of the shaft.

5. The device according to claim 1, wherein proximal to a distal portion of the shaft an opening or through-hole for a guidewire is arranged from the inner cavity or hollow space to the outside.

6. A device for the placement of an endovascular implant of at least partially cylindrical design into blood vessels, with the implant having an expanded state in which it is placed into the blood vessel and a compressed state in which it can be inserted into the blood vessel, wherein the device has an elongated shaft on the outside of which the implant is secured in the compressed state so as to be detachable, the elongated shaft having an inner cavity or hollow space extending in the longitudinal direction of the shaft and being permeable to a solvent where adhesive connection points are located, and said shaft extending through the implant, wherein the implant has at least one connection point to the shaft proximally and at least one connection point to the shaft distally, said connection points comprising an adhesive, and being chemically detachable by contacting the connection points with a solvent that dissolves the adhesive to such an extent that the implant is detached from the shaft and wherein a distal region of the shaft is composed at least partially of a coil which is formed from the helical configuration of a metal wire or a plastic thread, with the interspaces between the windings of the coil being permeable to a solvent.

7. The device according to claim 6, wherein the coil forming the distal region of the shaft is followed proximally by a region of the shaft which has a greater stiffness than the coil.

8. A device for the placement of an endovascular implant of at least partially cylindrical design into blood vessels, with the implant having an expanded state in which it is placed in the blood vessel, and a compressed state, in which it can be inserted into the blood vessel, wherein the device has an elongated shaft, on the outside of which the implant is detachably secured in the compressed state and with said shaft extending through the implant, wherein at least one thread extends in the longitudinal direction over the implant at least over a major portion of the length of the implant in such away that the implant is fixed on the shaft in the compressed state, wherein the thread has proximally and distally at least one connection point each to the shaft, of which at least one connection point comprises an adhesive and can be detached chemically by contacting said connection point with a solvent that dissolves the adhesive to such an extent that the thread is detached from the shaft, the elongated shaft having an inner cavity or hollow space extending in the longitudinal direction of the shaft and being permeable to a solvent at least in those sections where adhesive connection points are located and further including a delivery system for solvents, which extends at least temporarily through the inner cavity or hollow space of the shaft and through which a solvent can be applied to those locations of the shaft at which adhesive connection points are arranged on the outside of the shaft.

9. The device according to claim 8, wherein the at least one thread extends spirally in the longitudinal direction around the implant.

10. The device according to claim 8, wherein the distal connection point is chemically detachable.

11. The device according to claim 8 wherein the adhesive connection points comprise a polymer adhesive.

12. The device according to claim 8, wherein the inner cavity or hollow space extends from the proximal to the distal end of the shaft.

13. The device according to claim 8, wherein proximal to a distal portion of the shaft an opening or through-hole for a guidewire is arranged from the inner cavity or hollow space to the outside.

14. A device for the placement of an endovascular implant of at least partially cylindrical design into blood vessels, with the implant having an expanded state in which it is placed in the blood vessel, and a compressed state, in which it can be inserted into the blood vessel, wherein the device has an elongated shaft, on the outside of which the implant is detachably secured in the compressed state and with said shaft extending through the implant, wherein at least one thread extends in the longitudinal direction over the implant at least over a major portion of the length of the implant in such away that the implant is fixed on the shaft in the compressed state, wherein the thread has proximally and distally at least one connection point each to the shaft, of which at least one connection point comprises an adhesive and can be detached chemically by contacting said connection point with a solvent that dissolves the adhesive to such an extent that the thread is detached from the shaft, the elongated shaft having an inner cavity or hollow space extending in the longitudinal direction of the shaft and being permeable to a solvent at least in those sections where adhesive connection points are located and wherein a distal region of the shaft is composed at least partially of a coil which is formed from the helical configuration of a metal wire or a plastic thread, with the interspaces between the windings of the coil being permeable to a solvent.

15. The device according to claim 14, wherein the coil forming the distal region of the shaft is followed proximally by a region of the shaft which has a greater stiffness than the coil.

* * * * *